US011393249B2

(12) United States Patent
Lee et al.

(10) Patent No.: US 11,393,249 B2
(45) Date of Patent: Jul. 19, 2022

(54) APPARATUS AND METHOD OF PROVIDING VEHICLE SERVICE BASED ON INDIVIDUAL EMOTION RECOGNITION

(71) Applicants: HYUNDAI MOTOR COMPANY, Seoul (KR); KIA MOTORS CORPORATION, Seoul (KR)

(72) Inventors: Jin Mo Lee, Uiwang-si (KR); Young Bin Min, Busan (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 13 days.

(21) Appl. No.: 17/089,970

(22) Filed: Nov. 5, 2020

(65) Prior Publication Data

US 2022/0036049 A1 Feb. 3, 2022

(30) Foreign Application Priority Data

Jul. 29, 2020 (KR) ........................ 10-2020-0094340

(51) Int. Cl.
*G06V 40/16* (2022.01)
*B60K 28/06* (2006.01)
*A61B 5/16* (2006.01)

(52) U.S. Cl.
CPC ............ *G06V 40/174* (2022.01); *A61B 5/165* (2013.01); *B60K 28/06* (2013.01); *G06V 40/172* (2022.01)

(58) Field of Classification Search
CPC .... G06V 40/174; G06V 40/172; A61B 5/165; B60K 28/06
See application file for complete search history.

(56) References Cited

U.S. PATENT DOCUMENTS

| 7,027,621 | B1* | 4/2006 | Prokoski | G06K 9/00248 |
| | | | | 180/272 |
| 2016/0104486 | A1* | 4/2016 | Penilla | G10L 15/005 |
| | | | | 704/232 |
| 2017/0095192 | A1* | 4/2017 | Sadowsky | A61B 5/165 |
| 2019/0276036 | A1 | 9/2019 | Noguchi et al. | |
| 2020/0074154 | A1* | 3/2020 | el Kaliouby | A61B 5/7264 |

(Continued)

FOREIGN PATENT DOCUMENTS

| JP | 6648304 B2 | 2/2020 |
| KR | 10-1901417 B1 | 9/2018 |

*Primary Examiner* — Wesley J Tucker
(74) *Attorney, Agent, or Firm* — Morgan, Lewis & Bockius LLP

(57) ABSTRACT

Disclosed are an apparatus and method of providing a vehicle service based on individual emotion recognition for providing a vehicle service based on individually customized emotion recognition by learning emotion for each user. The apparatus includes a processor configured to determine whether an event occurs based on information on a driving environment and image acquirer configured to acquire a user facial image in response to event occurrence. The processor is further configured to learn user facial expression based on the user facial image in response to the event occurrence, and determine whether the user experiences specific emotion based on the learned user facial expression. The apparatus further includes a service provider configured to provide a vehicle service corresponding to the driving environment when determining that the user experiences the specific emotion.

18 Claims, 5 Drawing Sheets

(56) References Cited

U.S. PATENT DOCUMENTS

| | | | |
|---|---|---|---|
| 2020/0082188 A1* | 3/2020 | Singh | G06K 9/00832 |
| 2020/0082590 A1* | 3/2020 | Woo | G06V 40/28 |
| 2020/0207358 A1* | 7/2020 | Katz | G06F 3/017 |
| 2020/0215970 A1* | 7/2020 | Lee | B60H 1/00742 |
| 2020/0242421 A1* | 7/2020 | Sobhany | G06N 5/04 |
| 2021/0256542 A1* | 8/2021 | McDaniel | G06K 9/00302 |

* cited by examiner

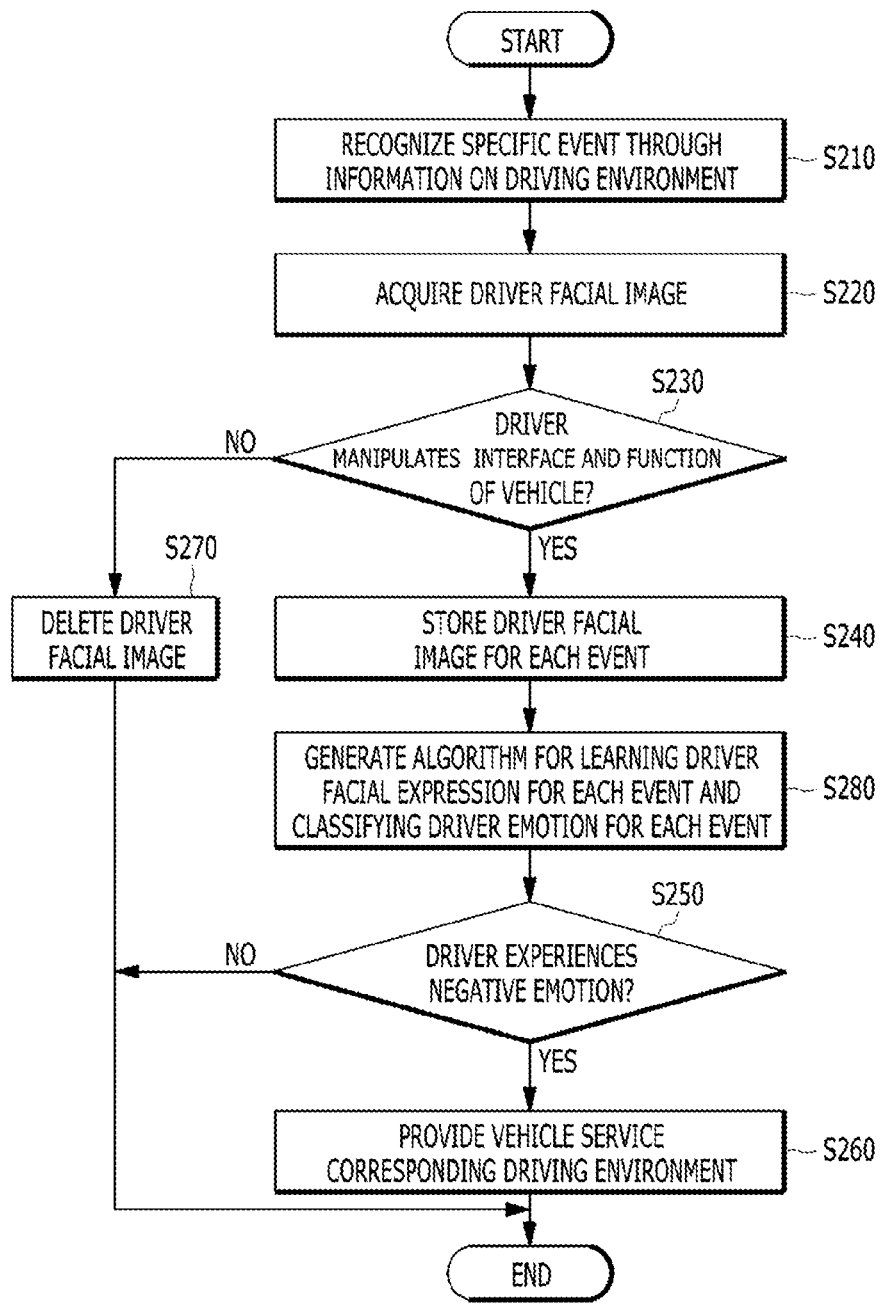

APPARATUS AND METHOD OF PROVIDING VEHICLE SERVICE BASED ON INDIVIDUAL EMOTION RECOGNITION

This application claims the benefit of Korean Patent Application No. 10-2020-0094340, filed on Jul. 29, 2020, which is hereby incorporated by reference as if fully set forth herein.

TECHNICAL FIELD

The present disclosure relates to an apparatus for providing a vehicle service based on individual emotion recognition, and more particularly, to an apparatus and method of providing a vehicle service based on individual emotion recognition for providing a vehicle service based on individually customized emotion recognition by learning emotion for each user.

BACKGROUND

In general, there are various driving environment factors causing a user to experience negative emotion, for example, traffic congestion, sudden stop, or offensive driving while traveling.

As such, when a driving environment is degraded to cause a user to experience negative emotion, vehicle control is adversely affected to cause accidents.

Recently, a vehicle service provision apparatus for providing a vehicle service appropriate for a user based on user emotion has been developed.

However, even if a driving environment factor causing negative emotion is generated, user emotion does not always change negatively.

That is, in the case of a driving environment factor that is frequently generated, if a vehicle service is provided to a user whenever the user recognizes the driving environment factor, the user is rather inconvenienced.

For example, when a user predicts traffic congestion, the user emotion does not change negatively even when a vehicle enters a traffic congestion state.

In addition, when the user feels good personally irrespective of vehicle driving, he or she may generously understand offensive driving of other people.

As such, even if a driving environment is unfavorable, when user emotion does not change negatively, it is desirable that a specific service is not provided to the user in a vehicle.

Accordingly, there has been a need for a vehicle serviced provision apparatus for accurately recognizing an actual emotion change of a user as well as detecting a driving environment and learning a method of expressing personal emotion to provide a vehicle required for the user.

SUMMARY

Accordingly, the present disclosure is directed to an apparatus and method of providing a vehicle service based on individual emotion recognition for improving convenience and safety by recognizing implicit emotion of a user based on user facial expression corresponding to a driving environment to provide a vehicle service.

The technical problems solved by the embodiments are not limited to the above technical problems and other technical problems which are not described herein will become apparent to those skilled in the art from the following description.

To achieve these objects and other advantages and in accordance with the purpose of the disclosure, as embodied and broadly described herein, an apparatus for providing a vehicle service includes a processor configured to determine whether an event occurs based on information on a driving environment, and an image acquiring device configured to acquire a user facial image in response to event occurrence. The processor is further configured to learn user facial expression based on the user facial image in response to the event occurrence, and determine whether the user experiences specific emotion based on the learned user facial expression. The apparatus further includes a service provider configured to provide a vehicle service corresponding to the driving environment when determining that the user experiences the specific emotion.

In another aspect of the present disclosure, a method of providing a vehicle service includes determining whether an event occurs based on information on a driving environment, by a processor, acquiring a user facial image in response to event occurrence, by an image acquiring device, learning user facial expression based on the user facial image in response to the event occurrence, by the processor, determining whether the user experiences specific emotion based on the learned user facial expression, by the processor, and providing a vehicle service corresponding to the driving environment when determining that the user experiences the specific emotion, by the service provider.

In another aspect of the present disclosure, a method of providing a vehicle service includes determining whether an event occurs in response to a driving environment, by a processor, acquiring a user facial image in response to event occurrence, by an image acquiring device, checking whether the user manipulates an interface and a function of a vehicle in response to the event occurrence, by the processor, when the user manipulates the interface and the function of the vehicle, learning user facial expression based on the user facial image in response to the event occurrence, by the processor, determining whether the user experiences specific emotion based on the learned user facial expression, by the processor, and providing a vehicle service corresponding to the driving environment when determining that the user experiences the specific emotion, by the service provider.

In another aspect of the present disclosure, a computer-readable recording medium having recorded thereon a program for executing a method of providing a vehicle service of a vehicle service provision apparatus based on individual emotion recognition performs procedures provided by the method of providing a vehicle service of a vehicle service provision apparatus based on individual emotion recognition.

In another aspect of the present disclosure, a vehicle includes a sensing apparatus configured to sense a driving environment, and a vehicle service provision apparatus configured to provide a vehicle service based on user facial expression corresponding to the driving environment. The vehicle service provision apparatus is configured to: acquire a user facial image in response to event occurrence when an event occurs in response to the driving environment, learn the user facial expression based on the user facial image in response to the event occurrence, determine whether the user experiences specific emotion based on the learned user facial expression, and provide a vehicle service corresponding to the driving environment when determining that the user experiences the specific emotion.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure. In the drawings:

FIG. 6 is a flowchart diagram for explaining a method of providing a vehicle service of a vehicle service provision apparatus according to a second embodiment of the present disclosure.

DETAILED DESCRIPTION

Figure 1:
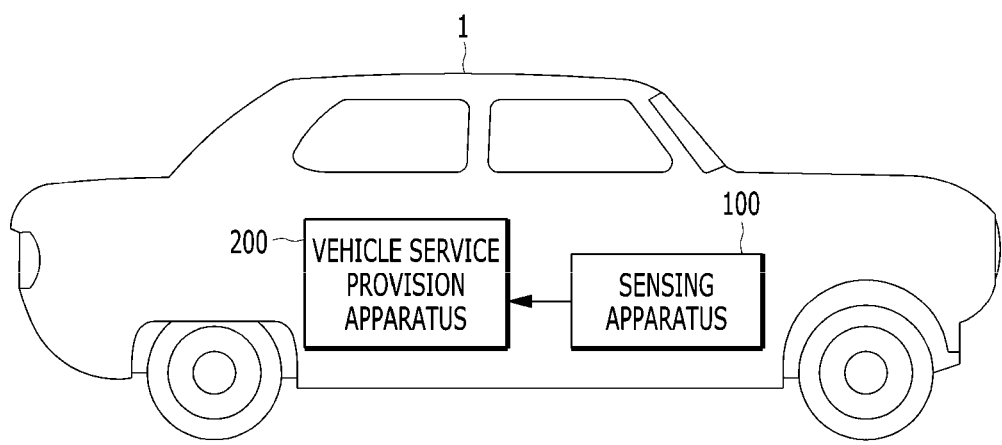
FIG. 1 is a diagram for explaining a vehicle including a vehicle service provision apparatus according to an embodiment of the present disclosure.

Exemplary embodiments of the present disclosure are described in detail so as for those of ordinary skill in the art to easily implement the present disclosure with reference to the accompanying drawings. However, the present disclosure may be implemented in various different forms and is not limited to these embodiments. To clearly describe the present disclosure, a part without concerning to the description is omitted in the drawings, and like reference numerals in the specification denote like elements.

Throughout the specification, one of ordinary skill would understand terms "include", "comprise", and "have" to be interpreted by default as inclusive or open rather than exclusive or closed unless expressly defined to the contrary. Further, terms such as "unit", "module", etc. disclosed in the specification mean units for processing at least one function or operation, which may be implemented by hardware, software, or a combination thereof.

Hereinafter, an apparatus and method of providing a vehicle service based on individual emotion recognition applicable to embodiments of the present disclosure will be described in detail with reference to FIGS. 1 to 6.

FIG. 1 is a diagram for explaining a vehicle including a vehicle service provision apparatus according to an embodiment of the present disclosure.

As shown in FIG. 1, a vehicle 1 according to the present disclosure may include a sensing apparatus 100 for sensing a driving environment, and a vehicle service provision apparatus 200 for providing a vehicle service based on user facial expression corresponding to a driving environment.

Here, when an event occurs in response to a driving environment, the vehicle service provision apparatus 200 may acquire a user facial image in response to event occurrence, may learn user facial expression based on the user facial image in response to event occurrence, may learn whether a user experiences negative emotion based on the learned user facial expression, and may provide a vehicle service corresponding to the driving environment when determining that the user experiences negative emotion.

The vehicle service provision apparatus 200 may monitor a driving environment based on information received from a sensor (e.g., an image sensor such as a camera, a lidar sensor, etc.) of a vehicle, and may generate an event corresponding to the monitored driving environment.

For example, the vehicle service provision apparatus 200 may generate an event when the monitored driving environment includes at least one of a traffic congestion situation, a sudden stop situation, a long-term deceleration situation, or an offensive driving situation, but the present disclosure is not limited thereto.

When learning user facial expression, the vehicle service provision apparatus 200 may analyze facial expression from the user facial image in response to event occurrence, may classify emotional expression corresponding to the analyzed facial expression, and may learn the user facial expression for each driving environment in conjunction with the classified emotional expression and an event corresponding thereto.

Here, when analyzing facial expression, the vehicle service provision apparatus 200 may calculate positiveness and excitability indexes from the user facial image, and may analyze facial expression based on the calculated positiveness and excitability indexes.

For example, when calculating the positiveness and excitability indexes, the vehicle service provision apparatus 200 may calculate the positiveness and excitability indexes based on a pre-stored emotion recognition algorithm.

For example, the vehicle service provision apparatus 200 may recognize user emotion as follows.

First, the vehicle service provision apparatus 200 may perform image-quality correction and noise removal on raw data, acquired through an image sensor (camera), through a preprocessing procedure, and may perform feature extraction such as extraction of emotion or movement on an input image.

Here, the present disclosure may use, as an emotion feature extraction method, a method of detecting feature by modeling or expressing the intensity of a pixel value in an entire facial image using a Holistic method.

The present disclosure may also use, as another emotion feature extraction method, a method of detecting feature by searching for the geometrical arrangement and position of feature from the face using a geometrical approach method.

As necessary, the present disclosure may also use, as another emotion feature extraction method, an active appearance model (AAM) method obtained by combining the aforementioned two feature extraction methods.

The vehicle service provision apparatus 200 may classify the state of a given image based on pattern classification of the extracted feature.

Here, a classification method may classify emotion using various methods such as a Bayesian network using a predefined conditional probability table (CPT), a K-nearest neighbor algorithm, or an artificial neural network.

Then, the vehicle service provision apparatus 200 may repeatedly classify a pattern of an image classified in multiple stages through a post processing procedure and may output the lastly selected result as the recognition result to terminate an emotion recognition procedure.

In another example, when learning the user facial expression, the vehicle service provision apparatus 200 may check whether a user manipulates an interface and a function of a vehicle in response to event occurrence, and when the user manipulates the interface and the function of the vehicle, the vehicle service provision apparatus 200 may analyze facial expression from the user facial image in response to event occurrence, may classify emotional expression corresponding to the classified facial expression, and may learn user facial expression for each driving environment in conjunction with the classified emotional expression and an event corresponding thereto.

Here, when checking whether the user manipulates the interface and the function of the vehicle, the vehicle service provision apparatus 200 may delete the acquired user facial image when the user does not manipulate the interface and the function of the vehicle.

When acquiring the user facial image in response to event occurrence, the vehicle service provision apparatus 200 may determine whether the user experiences negative emotion based on the user facial expression learned for each driving environment.

Here, when determining whether the user experiences negative emotion, the vehicle service provision apparatus 200 may determine whether the user experiences negative emotion based on the user facial expression learned for each driving environment when the user facial expression based on the acquired user facial image and the user facial expression learned for each driving environment are different from each other.

Then, when the vehicle service provision apparatus 200 provides a vehicle service, if the vehicle service provision apparatus 200 determines that the user experiences negative emotion, the vehicle service provision apparatus 200 may extract information on a vehicle service corresponding to the driving environment and may provide a vehicle service including at least one of a vehicle control service or a user convenience service based on the extracted information on the vehicle service.

When the vehicle service provision apparatus 200 provides a vehicle service, if the vehicle service provision apparatus 200 does not determine that the user experiences negative emotion, the vehicle service provision apparatus 200 may not provide a vehicle service corresponding to the driving environment.

As such, according to the present disclosure, average emotion information and an emotion recognition algorithm may be generated by learning all user facial expressions when an event occurs in response to a driving environment.

Thus, according to the present disclosure, the user does not always require a service when the event occurs in response to the driving environment, and thus, emotional expression that does not require a service may also be included in a learning target.

According to another embodiment of the present disclosure, emotion may also be classified by filtering an acquired facial image and learning only the emotional expression that requires a service.

Accordingly, according to the present disclosure, a facial image may be acquired when an event occurs, user manipulation of the interface and the function of the vehicle may be tracked and observed after the event occurs, and emotional expression corresponding to the facial image may be included in the learning target using the facial image only when the user manipulates the interface and the function of the vehicle.

When the user does not manipulate the interface and the function of the vehicle, the acquired facial image may be deleted.

In this case, according to the present disclosure, a time taken to acquire a facial image and to recognize whether a vehicle function manipulation command such as an infotainment function is generated for a predetermined time in order to determine whether the corresponding facial image is to be used in learning may be additionally required.

Here, according to the present disclosure, when emotional expression that does not require a service is few, there is no major problem in learning, but when emotional expression that does not require a service is great, a wrong learning result may be derived, and accordingly reliability needs to be increased to prevent the problem.

As such, the present disclosure may provide a vehicle service by recognizing implicit emotion of a user based on user facial expression corresponding to a driving environment, thereby improving convenience and safety.

The present disclosure may provide technology for providing a personalized user emotion recognition and customized emotion based service and may accurately recognize implicit emotion of the user by classifying user emotion based on user facial expression that mainly occurs when a specific driving environment occurs, thereby improving reliability.

As such, the present disclosure may provide an individually customized emotion recognition system but not a uniform emotion recognition system by considering that a method and a degree for expressing emotion are largely changed for each person.

Figure 2:
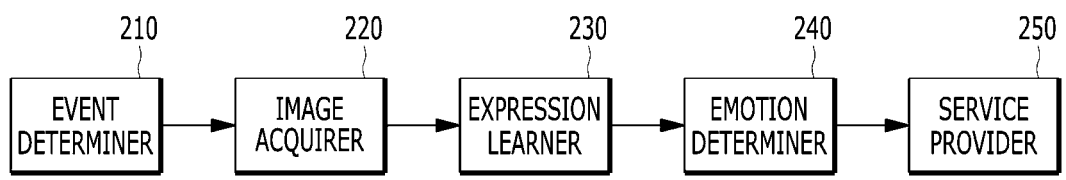
FIG. 2 is a block diagram showing the configuration of a vehicle service provision apparatus based on individual emotion recognition according to an embodiment of the present disclosure.

FIG. 2 is a block diagram showing the configuration of a vehicle service provision apparatus based on individual emotion recognition according to an embodiment of the present disclosure.

As shown in FIG. 2, the vehicle service provision apparatus 200 may include an event determiner 210 for generating an event in response to a driving environment, an image acquirer 220 for acquiring a user facial image in response to event occurrence, an expression learner 230 for learning user facial expression based on the user facial image in response to event occurrence, an emotion determiner 240 for determining whether a user experiences negative emotion based on the learned user facial expression, and a service provider 250 for providing a vehicle service corresponding to a driving environment when determining that the user experiences negative emotion.

Here, the event determiner 210 may monitor a driving environment based on information received from a sensor (e.g., an image sensor such as a camera, a lidar sensor, etc.) of a vehicle and may determine whether an event occurs in response to the monitored driving environment.

For example, the event determiner 210 may generate an event when the monitored driving environment includes at least one of a traffic congestion situation, a sudden stop situation, a long-term deceleration situation, or an offensive driving situation.

The image acquirer 220 may be installed in an indoor area of the vehicle and may include a camera for photographing the face of the user to acquire a facial image.

Then, the expression learner 230 may store a user facial image for each event based on the user facial image in response to event occurrence and, when the sufficient number of accumulated facial images are ensured, that is, when the number of stored facial images is equal to or greater than N, the expression learner 230 may generate an algorithm for learning facial expression of a driver for each event and classifying driver emotion for each event.

That is, the expression learner 230 may analyze the facial expression from the user facial image in response to event occurrence, may classify emotional expression corresponding to the analyzed facial expression, and may learn facial expression for each driving environment in conjunction with the classified emotional expression and an event corresponding thereto.

Here, when analyzing the facial expression, the expression learner 230 may calculate positiveness and excitability indexes from the user facial image and may analyze the facial expression based on the calculated positiveness and excitability indexes.

In this case, when calculating the positiveness and excitability indexes, the expression learner 230 may calculate the positiveness and excitability indexes based on the pre-stored emotion recognition algorithm.

As necessary, the expression learner 230 may check whether a user manipulates an interface and a function of a vehicle in response to event occurrence, and when the user manipulates the interface and the function of the vehicle, the expression learner 230 may analyze facial expression from the user facial image in response to event occurrence, may classify emotional expression corresponding to the classified facial expression, and may learn user facial expression for each driving environment in conjunction with the classified emotional expression and an event corresponding thereto.

Here, when checking whether the user manipulates the interface and the function of the vehicle, the expression learner 230 may delete the acquired user facial image when the user does not manipulate the interface and the function of the vehicle.

Then, when analyzing the facial expression, the expression learner 230 may calculate the positiveness and excitability indexes from the user facial image, and may analyze the facial expression based on the calculated positiveness and excitability indexes.

Here, when calculating the positiveness and excitability indexes, the expression learner 230 may calculate the positiveness and excitability indexes based on the pre-stored emotion recognition algorithm.

Then, when acquiring the user facial image in response to event occurrence, the emotion determiner 240 may determine whether the user experiences negative emotion based on the user facial expression learned for each driving environment.

Here, when determining whether the user experiences negative emotion, the emotion determiner 240 may determine whether the user experiences negative emotion based on the user facial expression learned for each driving environment when the user facial expression based on the acquired user facial image and the user facial expression learned for each driving environment are different from each other.

For example, when the user facial expression based on the acquired user facial image is positive emotion of the user and the user facial expression learned for each driving environment is negative emotion of the user, the emotion determiner 240 may determine that the user experiences negative emotion based on the user facial expression learned for each driving environment.

In another example, when the user facial expression based on the acquired user facial image is negative emotion of the user and the user facial expression learned for each driving environment is positive emotion of the user, the emotion determiner 240 may determine that the user experiences positive emotion based on the user facial expression learned for each driving environment.

When the service provider 250 provides a vehicle service (e.g., opening of a window, an operation of air conditioner, or multimedia/music playback), if the service provider 250 determines that the user experiences negative emotion, the service provider 250 may extract information on a vehicle service corresponding to the driving environment and may provide a vehicle service including at least one of a vehicle control service or a user convenience service based on the extracted information on the vehicle service. In one example, the service provider 250 may include a controller such as a processor configured to control components including, but not limited to, a speaker, a motor, a fan, an air conditioner, a GPS of the vehicle, so as to provide a vehicle service.

When the service provider 250 provides a vehicle service, if the service provider 250 does not determine that the user experiences negative emotion, the service provider 250 may not provide a vehicle service corresponding to the driving environment.

As such, there may be various driving environment factors causing a user to experience negative emotion, for example, traffic congestion, sudden stop, or offensive driving while traveling.

However, even if a driving environment factor causing negative emotion occurs, the driver may not always change negatively, and in the case of a driving environment factor that is frequently generated, if a vehicle service is provided to a user whenever the user recognizes the driving environment factor, the user may be rather inconvenienced.

For example, when the user predicts traffic congestion, the user emotion does not change negatively even when a vehicle enters a traffic congestion state, and when the user feels good personally irrespective of vehicle driving, he or she may generously understand offensive driving of other people.

In this case, a need to particularly provide a service in a vehicle may be low.

Accordingly, according to the present disclosure, for the aforementioned reason, it may be important to recognize an actual change in user emotion along with detection of a driving environment and to recognize a situation that occurs along with the change in user emotion.

However, a method of expressing individual negative emotion by a driver is different for each driver, and accordingly according to the present disclosure, driver emotion may be recognized through facial expression and the method of expressing individual emotion may be learned.

That is, according to the present disclosure, negative emotion may be detected using technology for recognizing emotion of facial expression.

For example, according to the present disclosure, when specific emotion occurs based on emotion classification (joy, sorrow, anger, surprise, misery, and disgust), a vehicle control and service corresponding to the specific emotion may be provided.

For example, according to the present disclosure, when negative emotion of the user, such as sadness, is recognized in response to a driving environment such as traffic congestion, a vehicle service such as a bypass may be provided.

According to the present disclosure, a method of expressing facial expression of a driver who expresses negative emotion may be individually learned.

For example, when a traffic congestion situation or a sudden stop situation occurs, even if the user implicitly experiences languidness or surprise, he or she may express opposite facial expression such as hollow laugh or smile.

The user facial expression such as hollow laugh or smile does not correspond to a situation in which the user experiences substantial pleasant emotion, and thus according to the present disclosure, the reliability of providing a service may be improved by obviously differentiating and recognizing an expression method such as fake laugh and genuine laugh.

Accordingly, according to the present disclosure, unnecessary service provision may be reduced and only a service required by a user may be provided by learning facial expression corresponding to a specific driving environment situation for each individual user and classifying emotion corresponding to a driving environment situation for each individual user.

Figure 3:
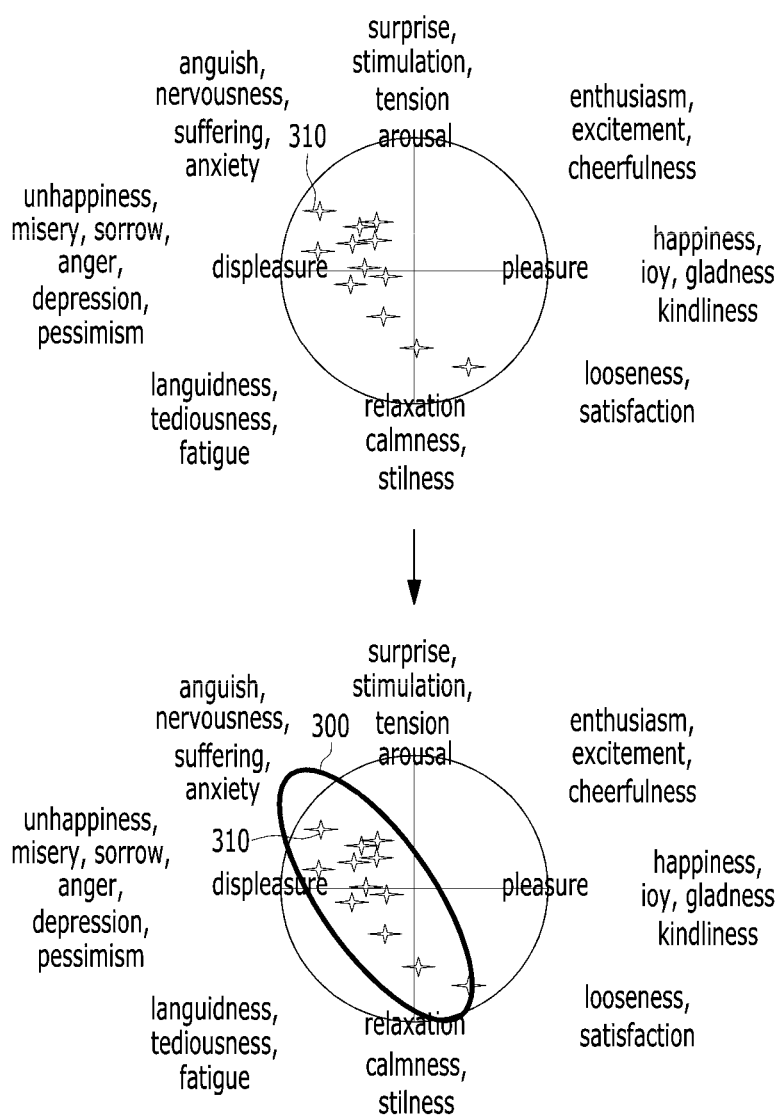
FIG. 3 is a diagram for explaining a procedure of learning user facial expression in response to event occurrence.

FIG. 3 is a diagram for explaining a procedure of learning user facial expression in response to event occurrence.

As shown in FIG. 3, according to the present disclosure, when user facial expression is learned, facial expression may be analyzed from the user facial image in response to event occurrence, emotional expression corresponding to the analyzed facial expression may be classified, and the user facial expression may be learned for each driving environment in conjunction with the classified emotional expression and an event corresponding thereto.

Here, according to the present disclosure, when the facial expression is analyzed, a positiveness-excitability index 310 may be calculated from the user facial image, and the facial expression may be analyzed based on the calculated positiveness-excitability index 310.

As shown in FIG. 3, a plurality of pieces of information on emotion corresponding to occurrence of a specific driving event based on the positiveness-excitability index 310 may be acquired through traveling performed a plurality of number of times, the positiveness-excitability index 310 in the specific range may be grouped based on the acquired pieces of information on emotion, and a corresponding emotion index group 300 may be classified into specific emotion to recognize user emotion.

As such, according to the present disclosure, user emotion may be recognized as follows.

First, according to the present disclosure, image-quality correction and noise removal may be performed on raw data, acquired through an image sensor (camera), through a preprocessing procedure, and feature extraction such as extraction of emotion or movement may be performed on an input image.

Here, the present disclosure may use, as an emotion feature extraction method, a method of detecting feature by modeling or expressing the intensity of a pixel value in an entire facial image using a Holistic method.

The present disclosure may also use, as another emotion feature extraction method, a method of detecting feature by searching for the geometrical arrangement and position of feature from the face using a geometrical approach method.

As necessary, the present disclosure may also use, as another emotion feature extraction method, an active appearance model (AAM) method obtained by combining the aforementioned two feature extraction methods.

According to the present disclosure, the state of a given image may be classified based on pattern classification of the extracted feature.

Here, a classification method may classify emotion using various methods such as a Bayesian network using a predefined conditional probability table (CPT), a K-nearest neighbor algorithm, or an artificial neural network.

Then, a pattern of an image classified in multiple stages through a post processing procedure may be repeatedly classified and the lastly selected result as the recognition result may be output to terminate an emotion recognition procedure.

As such, according to the present disclosure, average emotion information and an emotion recognition algorithm may be generated by learning all user facial expressions when an event occurs in response to a driving environment.

Figure 4A:
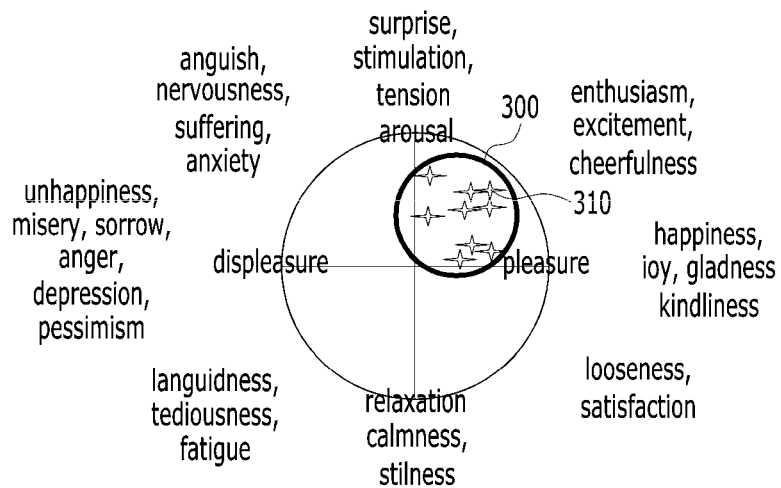
FIGS. 4A and 4B are diagrams showing positiveness and excitability indexes indicating a change in user emotion depending on a driving environment.
Figure 4B:
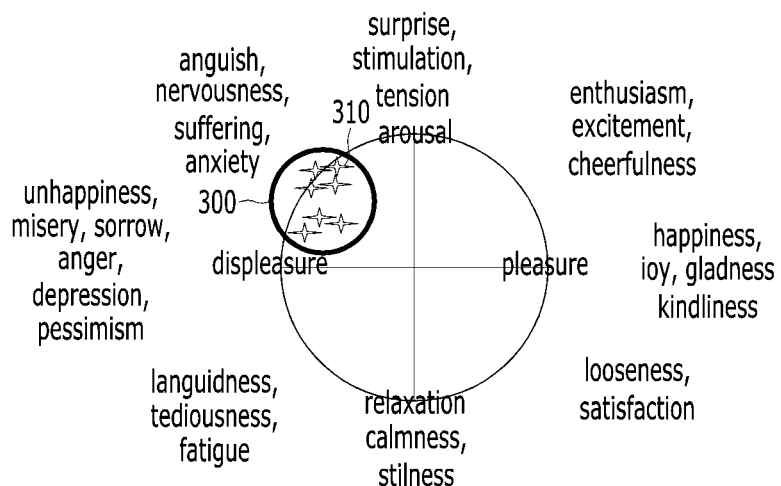

FIGS. 4A and 4B are diagrams showing positiveness and excitability indexes indicating a change in user emotion depending on a driving environment.

As shown in FIGS. 4A and 4B, according to the present disclosure, when the user facial image may be acquired in response to event occurrence, whether the user experiences negative emotion based on the user facial expression learned for each driving environment may be determined.

Here, according to the present disclosure, when the user facial expression based on the acquired user facial image and the user facial expression learned for each driving environment are different from each other, whether the user experiences negative emotion may be determined based on the user facial expression learned for each driving environment.

For example, according to the present disclosure, when the user facial expression based on the acquired user facial image is positive emotion of the user and the user facial expression learned for each driving environment is negative emotion of the user, it may be determined that the user experiences negative emotion based on the user facial expression learned for each driving environment.

In another example, when the user facial expression based on the acquired user facial image is negative emotion of the user and the user facial expression learned for each driving environment is positive emotion of the user, it may be determined that the user experiences positive emotion based on the user facial expression learned for each driving environment.

As shown in FIGS. 4A and 4B, according to the present disclosure, the emotion index group 300 corresponding to the positiveness-excitability index 310 may be classified into specific emotion to recognize user emotion.

For example, as shown in FIG. 4A, when the user has surprised expression or hollow laugh expression in a traffic congestion situation, it may be learned that emotion change is expressed through surprise or laugh expression corresponding to the traffic congestion situation.

According to the present disclosure, when the learned user emotion changes in the traffic congestion situation, a service such as guidance to a bypass may be provided.

In contrast, according to the present disclosure, when the user has angry expression and sad expression in the traffic congestion situation, it may be determined that the current expression is not general emotional expression of the user for expressing the traffic congestion situation and a service may not be provided.

That is, according to the present disclosure, it may be determined that angry expression and sad expression of the user accidently occur at a time of the traffic congestion situation and the current expression is emotional expression of the user for different reason irrespective of the traffic congestion situation.

As necessary, as shown in FIG. 4B, when the user has contemptuous, sad, or angry expression in the traffic congestion, it may be learned that emotion change is expressed through contemptuous, sad, or angry expression corresponding to the traffic congestion situation.

According to the present disclosure, when the learned user emotion changes in the traffic congestion situation, a service such as guidance to a bypass may be provided.

In contrast, according to the present disclosure, when the user has laughing expression in the traffic congestion situation, it may be determined that the current expression is not general emotional expression of the user for expressing the traffic congestion situation and a service may not be provided.

That is, according to the present disclosure, it may be determined that laughing expression of the user accidently occur at a time of the traffic congestion situation and the current expression is emotional expression of the user for different reason irrespective of the traffic congestion situation.

Figure 5:
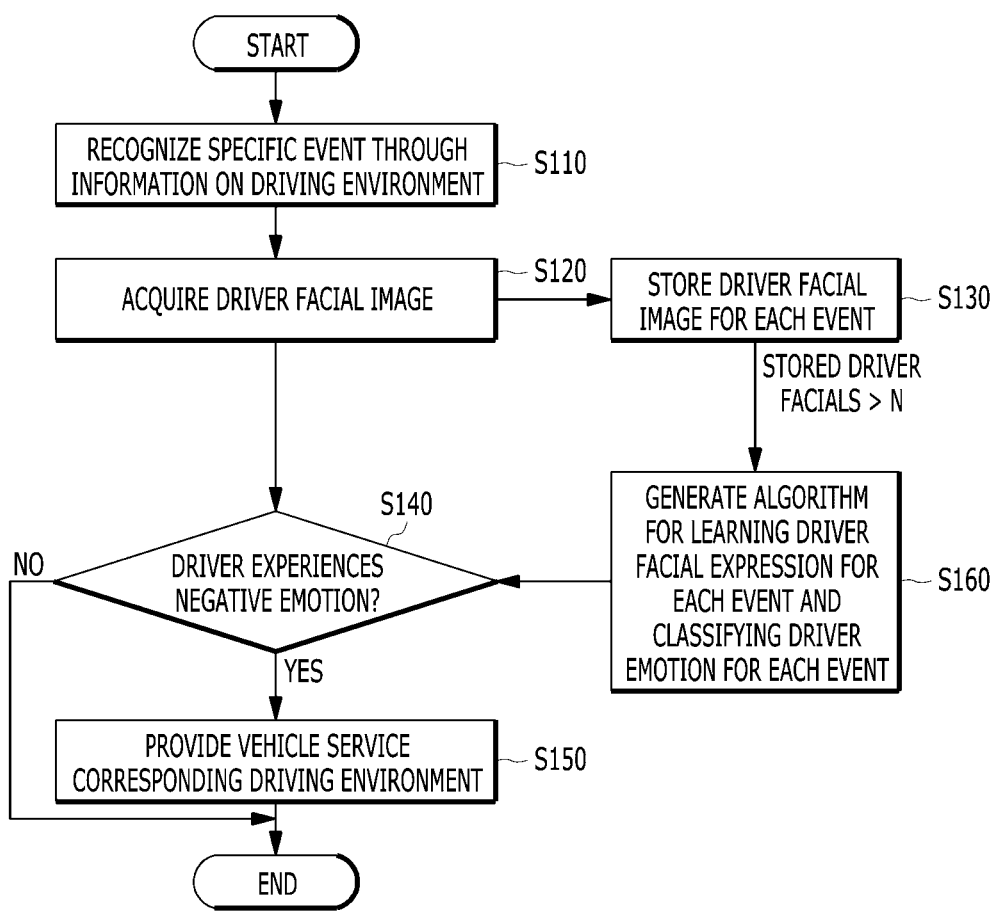
FIG. 5 is a flowchart diagram for explaining a method of providing a vehicle service of a vehicle service provision apparatus according to a first embodiment of the present disclosure.

FIG. 5 is a flowchart diagram for explaining a method of providing a vehicle service of a vehicle service provision apparatus according to a first embodiment of the present disclosure.

As shown in FIG. 5, according to the present disclosure, a specific event may be recognized through information on a driving environment (S110).

Here, according to the present disclosure, the driving environment may be monitored based on information received from a sensor (e.g., an image sensor such as a camera, a lidar sensor, etc.) of a vehicle, and a specific event may be recognized through information on the monitored driving environment.

According to the present disclosure, a user facial image may be acquired in response to event occurrence (S120).

Then, according to the present disclosure, a user facial image for each event based on the user facial image in response to event occurrence may be stored (S130).

When the sufficient number of accumulated facial images are ensured, that is, when the number of stored facial images is equal to or greater than N, an algorithm for learning facial expression of a driver for each event and classifying driver emotion for each event may be generated (S160). In one example, N is a predetermined natural number. For example, N is 3, 4, 5, or greater.

Here, according to the present disclosure, the facial expression from the user facial image in response to event occurrence may be analyzed, emotional expression corresponding to the analyzed facial expression may be classified, and facial expression for each driving environment may be learned in conjunction with the classified emotional expression and an event corresponding thereto.

For example, according to the present disclosure, positiveness and excitability indexes may be calculated from the user facial image, and the facial expression may be analyzed based on the calculated positiveness and excitability indexes.

Then, according to the present disclosure, whether the user experiences negative emotion may be determined based on the learned user facial expression (S140).

Here, when the user facial image in response to event occurrence is acquired, whether the user experiences negative emotion may be determined based on the user facial expression learned for each driving environment.

For example, according to the present disclosure, whether the user experiences negative emotion may be determined based on the user facial expression learned for each driving environment when the user facial expression based on the acquired user facial image and the user facial expression learned for each driving environment are different from each other.

According to the present disclosure, when it is determined that the user experiences negative emotion, a vehicle service corresponding to the driving environment may be provided (S150).

Here, according to the present disclosure, when it is determined that the user experiences negative emotion, information on a vehicle service corresponding to the driving environment may be extracted, and a vehicle service including at least one of a vehicle control service or a user convenience service may be provided based on the extracted information on the vehicle service.

According to the present disclosure, when it is determined that the user does not experience negative emotion, a vehicle service corresponding to the driving environment may not be provided.

FIG. 6 is a flowchart diagram for explaining a method of providing a vehicle service of a vehicle service provision apparatus according to a second embodiment of the present disclosure.

As shown in FIG. 6, according to the present disclosure, a specific event may be recognized through information on a driving environment (S210).

Here, according to the present disclosure, the driving environment may be monitored based on information received from a sensor of a vehicle, and a specific event may be recognized through information on the monitored driving environment.

According to the present disclosure, a user facial image may be acquired in response to event occurrence (S220).

Then, according to the present disclosure, whether a user manipulates an interface and a function of a vehicle in response to event occurrence may be checked (S230).

Then, according to the present disclosure, when the user manipulates the interface and the function of the vehicle, a user facial image for each event based on the user facial image in response to event occurrence may be stored (S240).

When the sufficient number of accumulated facial images are ensured, that is, when the number of stored facial images is equal to or greater than n, an algorithm for learning facial expression of a driver for each event and classifying driver emotion for each event may be generated (S280).

Here, according to the present disclosure, when the user manipulates the interface and the function of the vehicle, the facial expression from the user facial image in response to event occurrence may be analyzed, emotional expression corresponding to the analyzed facial expression may be classified, and facial expression for each driving environment may be learned in conjunction with the classified emotional expression and an event corresponding thereto.

For example, according to the present disclosure, positiveness and excitability indexes may be calculated from the user facial image, and the facial expression may be analyzed based on the calculated positiveness and excitability indexes.

According to the present disclosure, when the user does not manipulate the interface and the function of the vehicle, the acquired facial image may be deleted (S270).

Then, according to the present disclosure, whether the user experiences negative emotion may be determined based on the user facial expression learned for each driving environment (S250).

Here, according to the present disclosure, when the user facial image in response to event occurrence is acquired, whether the user experiences negative emotion may be determined based on the user facial expression learned for each driving environment.

For example, according to the present disclosure, when the user facial expression based on the acquired user facial image and the user facial expression learned for each driving environment are different from each other, whether user experiences negative emotion may be determined based on the user facial expression learned for each driving environment.

According to the present disclosure, when it is determined that that the user experiences negative emotion, a vehicle service corresponding to the driving environment may be provided (S260).

Here, according to the present disclosure, when it is determined that the user experiences negative emotion, information on a vehicle service corresponding to the driving environment may be extracted, and a vehicle service including at least one of a vehicle control service or a user convenience service may be provided based on the extracted information on the vehicle service.

According to the present disclosure, when it is not determined that the user experiences negative emotion, a vehicle service corresponding to the driving environment may not be provided.

According to the present disclosure, a computer-readable recording medium, such as a non-transitory computer-readable recording medium, having recorded thereon a program for executing a method of providing a vehicle service of a vehicle service provision apparatus based on individual emotion recognition may perform procedures provided by the method of providing a vehicle service of a vehicle service provision apparatus based on individual emotion recognition.

As such, the present disclosure may provide a vehicle service by recognizing implicit emotion of a user based on user facial expression corresponding to a driving environment, thereby improving convenience and safety.

The present disclosure may provide technology for providing a personalized user emotion recognition and customized emotion based service and may accurately recognize implicit emotion of the user by classifying user emotion based on user facial expression that mainly occurs when a specific driving environment occurs, thereby improving reliability.

As such, the present disclosure may provide a individually customized emotion recognition system but not a uniform emotion recognition system by considering that a method and a degree for expressing emotion are largely changed for each person.

The method of providing a vehicle service of a vehicle service provision apparatus based on individual emotion recognition related to at least one embodiment of the present disclosure as configured above may provide a vehicle service by recognizing implicit emotion of a user based on user facial expression corresponding to a driving environment, thereby improving convenience and safety.

The present disclosure may provide technology for providing a personalized user emotion recognition and customized emotion based service and may accurately recognize implicit emotion of the user by classifying user emotion based on user facial expression that mainly occurs when a specific driving environment occurs, thereby improving reliability.

As such, the present disclosure may provide a individually customized emotion recognition system but not a uniform emotion recognition system by considering that a method and a degree for expressing emotion are largely changed for each person.

It will be appreciated by persons skilled in the art that that the effects that could be achieved with the present disclosure are not limited to what has been particularly described hereinabove and other advantages of the present disclosure will be more clearly understood from the detailed description.

The aforementioned present disclosure can also be embodied as computer-readable code stored on a computer-readable recording medium, such as a non-transitory computer-readable recording medium. For example, the method or the operations performed by the vehicle service provision apparatus 200 and/or the individual components thereof can be embodied as computer readable code stored on a memory implemented by, for example, a computer readable recording medium such as a non-transitory computer readable recording medium. The computer-readable recording medium is any data storage device that can store data which can thereafter be read by a computer. Examples of the computer-readable recording medium include a hard disk drive (HDD), a solid state drive (SSD), a silicon disc drive (SDD), read-only memory (ROM), random-access memory (RAM), CD-ROM, magnetic tapes, floppy disks, optical data storage devices, etc. In one example, the vehicle service provision apparatus 200 may include a computer, a processor, or a microprocessor. When the computer, the processor, or the microprocessor reads and executes the computer readable code stored in the computer readable recording medium, the computer, the processor, or the microprocessor may be configured to perform the above-described operations/method. Alternatively, the event determiner 210, the expression learner 230, the emotion determiner 240, and the service provider 250, each, or together, may include a computer, a processor, or a microprocessor. When the computer, the processor, or the microprocessor reads and executes the computer readable code stored in the computer readable recording medium, the computer, the processor, or the microprocessor may be configured to perform the above-described operations/method in conjunction with the image acquirer 220.

It will be apparent to those skilled in the art that various modifications and variations can be made in the present disclosure without departing from the spirit or scope of the embodiments. Thus, it is intended that the present disclosure cover the modifications and variations of the embodiment provided they come within the scope of the appended claims and their equivalents.

What is claimed is:

1. An apparatus for providing a vehicle service, the apparatus comprising:
a processor configured to determine whether an event occurs based on information on a driving environment; and
an image acquiring device configured to acquire a user facial image in response to event occurrence;
wherein the processor is further configured to:
learn user facial expression based on the user facial image in response to the event occurrence; and
determine whether the user experiences specific emotion based on the learned user facial expression,
the apparatus further comprises a service provider configured to provide a vehicle service corresponding to the driving environment when determining that the user experiences the specific emotion,
the processor checks whether the user manipulates an interface and a function of a vehicle in response to the event occurrence, and
when the user manipulates the interface and the function of the vehicle, the processor analyzes facial expression from the user facial image in response to the event occurrence, classifies emotional expression corresponding to the analyzed facial expression, and learns user facial expression for each driving environment in conjunction with the classified emotional expression and an event corresponding thereto.

2. The apparatus of claim 1, wherein the processor monitors the driving environment based on information received from a sensor of a vehicle and determines whether the event occurs in response to the monitored driving environment.

3. The apparatus of claim 1, wherein the image acquiring device is installed in an indoor area of a vehicle and comprises a camera configured to photograph a face of the user to acquire the user facial image.

4. The apparatus of claim 1, wherein, when analyzing the facial expression, the processor calculates positiveness and excitability indexes from the user facial image, and analyzes the facial expression based on the calculated positiveness and excitability indexes.

5. The apparatus of claim 1, wherein, when checking whether the user manipulates the interface and the function of the vehicle, the processor deletes the acquired user facial image when the user does not manipulate the interface and the function of the vehicle.

6. The apparatus of claim 1, wherein, when acquiring the user facial image in response to the event occurrence, the processor determines whether the user experiences the specific emotion based on the user facial expression learned for each driving environment.

7. The apparatus of claim 1, wherein, when determining whether the user experiences the specific emotion, the processor determines whether the user experiences the specific emotion based on the user facial expression learned for each driving environment when the user facial expression based on the acquired user facial image and the user facial expression learned for each driving environment are different from each other.

8. The apparatus of claim 1, wherein, when the vehicle service is provided, if determining that the user experiences the specific emotion, the service provider extracts information on the vehicle service corresponding to the driving environment and provides a vehicle service comprising at least one of a vehicle control service or a user convenience service based on the extracted information on the vehicle service.

9. The apparatus of claim 1, wherein, when the vehicle service is provided, if determining that the user does not experience the specific emotion, the service provider does not provide the vehicle service corresponding to the driving environment.

10. A method of providing a vehicle service, the method comprising:
determining whether an event occurs based on information on a driving environment, by a processor;
acquiring a user facial image in response to event occurrence, by an image acquiring device;
learning user facial expression based on the user facial image in response to the event occurrence, by the processor;
determining whether the user experiences specific emotion based on the learned user facial expression, by the processor; and
providing a vehicle service corresponding to the driving environment when determining that the user experiences the specific emotion, by a service provider,
wherein the learning the user facial expression comprises:
checking whether the user manipulates an interface and a function of a vehicle in response to the event occurrence,
when the user manipulates the interface and the function of the vehicle, learning user facial expression based on the user facial image in response to the event occurrence, and
classifying emotional expression corresponding to the learned facial expression, and learning user facial expression for each driving environment in conjunction with the classified emotional expression and an event corresponding thereto.

11. The method of claim 10, wherein the determining whether the event occurs based on the information on the driving environment comprises monitoring the driving environment based on information received from a sensor of a vehicle and determining whether the event occurs in response to the monitored driving environment.

12. The method of claim 10, wherein the determining whether the user experiences the specific emotion comprises, when acquiring the user facial image in response to the event occurrence, determining whether the user experiences the specific emotion based on the user facial expression learned for each driving environment.

13. A method of providing a vehicle service, the method comprising:
determining whether an event occurs in response to a driving environment, by a processor;
acquiring a user facial image in response to event occurrence, by an image acquiring device;
checking whether the user manipulates an interface and a function of a vehicle in response to the event occurrence, by the processor;
when the user manipulates the interface and the function of the vehicle, learning user facial expression based on the user facial image in response to the event occurrence, by the processor;
determining whether the user experiences specific emotion based on the learned user facial expression, by the processor; and
providing a vehicle service corresponding to the driving environment when determining that the user experiences the specific emotion, by a service provider.

14. The method of claim 13, wherein the learning the user facial expression comprises: when the user manipulates the interface and the function of the vehicle, analyzing facial expression from the user facial image in response to the event occurrence, classifying emotional expression corresponding to the analyzed facial expression, and learning user facial expression for each driving environment in conjunction with the classified emotional expression and an event corresponding thereto.

15. The method of claim 13, wherein the learning the user facial expression comprises, when checking whether the user manipulates the interface and the function of the vehicle, deleting the acquired user facial image when the user does not manipulate the interface and the function of the vehicle.

16. A non-transitory computer-readable recording medium having recorded thereon a program for executing the method of claim 13.

17. A vehicle comprising:
a sensing apparatus configured to sense a driving environment; and
a vehicle service provision apparatus configured to provide a vehicle service based on user facial expression corresponding to the driving environment,
wherein the vehicle service provision apparatus is configured to: acquire a user facial image in response to event occurrence when an event occurs in response to the driving environment, learn the user facial expression based on the user facial image in response to the event occurrence, determine whether the user experiences specific emotion based on the learned user facial expression, and provide a vehicle service corresponding to the driving environment when determining that the user experiences the specific emotion, and the vehicle service provision apparatus checks whether the user manipulates an interface and a function of a vehicle in response to the event occurrence, and when the user manipulates the interface and the function of the vehicle, the processor analyzes facial expression from the user facial image in response to the event occurrence, classifies emotional expression corresponding to the analyzed facial expression, and learns user facial expression for each driving environment in conjunction with the classified emotional expression and an event corresponding thereto.

18. A non-transitory computer-readable recording medium having recorded thereon a program for executing the method of claim 10.

* * * * *